United States Patent
Prabhune et al.

(10) Patent No.: US 9,757,481 B2
(45) Date of Patent: Sep. 12, 2017

(54) FLUORESCENT, SPHERICAL SOPHOROLIPID MESOSTRUCTURES FOR IMAGING AND THERAPEUTIC APPLICATIONS

(71) Applicant: Council of Scientific & Industrial Research, New Delhi (IN)

(72) Inventors: Asmita Ashutosh Prabhune, Maharashtra (IN); Pradeep Kumar Singh, Maharashtra (IN); Ruchira Arup Mukherji, Maharashtra (IN); Satishchandra Balkrishna Ogale, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 39 days.

(21) Appl. No.: 14/398,115

(22) PCT Filed: Apr. 30, 2013

(86) PCT No.: PCT/IB2013/053394
§ 371 (c)(1),
(2) Date: Oct. 30, 2014

(87) PCT Pub. No.: WO2013/164758
PCT Pub. Date: Nov. 7, 2013

(65) Prior Publication Data
US 2015/0139910 A1 May 21, 2015

(30) Foreign Application Priority Data
Apr. 30, 2012 (IN) .......................... 1314/DEL/2012

(51) Int. Cl.
*A61K 49/18* (2006.01)
*A61K 41/00* (2006.01)
*A61K 49/00* (2006.01)
*A61K 9/00* (2006.01)
*A61K 9/50* (2006.01)

(52) U.S. Cl.
CPC ........ *A61K 49/1818* (2013.01); *A61K 9/0009* (2013.01); *A61K 9/5094* (2013.01); *A61K 41/0052* (2013.01); *A61K 49/0065* (2013.01); *Y10T 428/2982* (2015.01)

(58) Field of Classification Search
CPC ............ A61K 41/0052; A61K 49/0065; A61K 9/0009; A61K 9/5094; A61K 49/1818; Y10T 428/2982
See application file for complete search history.

(56) References Cited

PUBLICATIONS

Baccile, N. et al. 2010 "Sophorolipids: a yeast-derived glycolipids as greener structure directing agents for self-assembled nanomaterials" *Green Chemistry* 12: 1564-1567.
Pradeep, K.S. et al. 2013 "Fluorescent sophorolipid molecular assembly and its magnetic nanoparticle loading: a pulsed laser process" *Green Chemistry* 15: 943-953.
Wang, Y. et al. 2007 "Photocontrolled reversible supramolecular assemblies of an azobenzene-containing surfactant with α-cyclodextrin" *Angew Chem Int Ed* 46: 2823-2826.

*Primary Examiner* — Robert Cabral
(74) *Attorney, Agent, or Firm* — Knobbe, Martens, Olson & Bear, LLP

(57) ABSTRACT

UV-Laser-synthesized, fluorescent, spherical and magnetic nanoparticles are loaded Sophorolipid mesostructures useful for bio-imaging and therapeutic applications.

9 Claims, 9 Drawing Sheets

US 9,757,481 B2

FLUORESCENT, SPHERICAL SOPHOROLIPID MESOSTRUCTURES FOR IMAGING AND THERAPEUTIC APPLICATIONS

TECHNICAL FIELD OF THE INVENTION

This invention relates to fluorescent, spherical Sophorolipid mesostructures useful for imaging and therapeutic applications. Particularly, present invention relates to process for the preparation of fluorescent, spherical Sophorolipid mesostructures by irradiating UV laser pulse. More particularly, present invention relates to fluorescent, spherical and magnetic nanoparticles loaded Sophorolipid mesostructures and process for the preparation thereof by irradiating UV laser pulse.

BACKGROUND AND PRIOR ART OF THE INVENTION

Bio-imaging vehicles which can absorb light and facilitate fluorescent or colorimetric detection are of fundamental significance to various medical applications such as photothermal (W. C. W. Chan and S. Nie, Science, 1998; J. F. Lovell et al. Nat. Mater., 2011) or photo-dynamic therapy. Inorganic nanoparticles, especially quantum dots (R. Weissleder, Science, 2006) absorb light strongly and posses good luminescence properties, making them suitable vehicles for such applications domains. Yet one does not witness their widespread use in medical applications possibly because of their limited drug loading capability restricted only to the nanoparticles surface and inherent high level of toxicity. Another serious problem faced when using such inorganic nanomaterials (e.g. iodine, gadolinium, and radioisotopes) as contrasting agent[9] in magnetic imaging is their unduly long residence time in the body long after the delivery procedure and higher noise to target signal ratio. To overcome these disadvantages, bio-organic nanoparticles are now being extensively used in therapeutics and for diagnostic imaging because of their much higher drug loading capacity, perfect biocompatibility and controlled activation under specific conditions such as pH, temperature etc. Biosurfactants derived from microbes are an interesting category of bio-organic systems with potential for applicability in biomedicine. They can be produced from renewable feedstock or waste material (A. Daverey et al. World Acad. Sci., Eng. Technol 2009) by a natural fermentation. Such micro-organism derived biosurfactants are also structurally very diverse. Moreover, they are readily degradable and display low toxicity. These properties are clearly desirable over those of traditional surfactants which can be eco-toxic, susceptible to bio-accumulation and generally averse to biodegradability. Some traditional surfactants with improved environmental performance such as alkyl polyglucosides, alkyl polyglucamides and fatty ester methyl ester ethoxylates are in use. However they are not necessarily made from renewable resources and may involve partial chemical processing.

A number of biosurfactants such as rhamnolipids (*Pseudomonas aeruginosa*), sophorolipids (*Candida bombicola*), trehalose lipids, cellobiose lipids, mannosylerythritol lipids, surfactin (*Bacillus subtilis*) and emulsan (*Acinetobacter calcoaceticus*) have been subjected to different scientific studies. Apart from surfactin and emulsan, all others are glycolipids which are easily the most important class of biosurfactants. Sophorolipid (J. H. Fuhrhop and T. Wang, Chem. Rev., 2004) are amphiphilic molecules which contain both hydrophobic (nonpolar) and hydrophilic (polar) groups. This character enables them to reduce the surface and interfacial energies leading to formation of emulsions. The foremost reasons for a high and increasing level of interest in Sophorolipid is due to their biodegradability and low toxicity as well as their unique structures that can facilitate their engineering to suit a specific application domain. Also, sophorolipids are easily synthesized by non-pathogenic yeast using very cost effective resources.

When dissolved in water, Sophorolipid molecules can form micelles-like structures. Some literature reports also discuss supramolecular assemblies of Sophorolipid monolayer vesicles, helical fibers/ribbons/tubules, and even rigid rods.

In current biomedical scenario optically active nanomaterials hold great promise in the context of advancement of a range of biophotonic and photocoustic techniques via nanoscale optical effects and synergistic integration of multiple imaging and therapeutics. Towards this end fluorescent nanoparticles are of immense significance because they facilitate multiple bio-imaging and therapeutic modulations. Inorganic nanomaterials such as quantum dots with intrinsic fluorescence properties have several disadvantages for such applications including toxicity. A cursory review of prior art indicates that despite the availability and unique characters of Sophorolipid, the applications of the same is not scaled for biomedical applications such as imaging.

Therefore, there is a need in the art to provide sophorolipid based mesoscale and biocompatible molecular self-assembled structures that show remarkable fluorescence that can be scaled for biomedical applications.

OBJECTS OF THE INVENTION

Main object of the present invention is to provide laser induced self-assembled vesicular mesostructures of biosynthesized Sophorolipid useful for bio-imaging and therapeutic applications.

SUMMARY OF THE INVENTION

Figure 1:
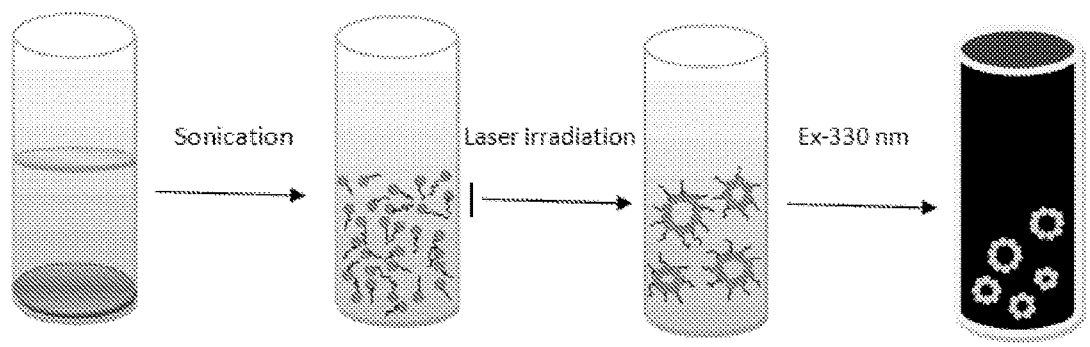
FIG. 1 represents schematic of Sophorolipid (SL) mesostructure formation.

Accordingly, the present invention provides fluorescent and highly spherical mesoscale sophorolipid mesostructure having size in the range of 100-300 nm, characterized by NMR double triplet signature at δ (ppm): 5.34 as well as at 5.37 in CDCl3, TMS, 400 Hz; an intense peak at 1630 cm-1 in FTIR; the characteristic peaks at 130.24 and 130.36 ppm in 13C NMR, indicating the extra C=C bond.

In one embodiment of the present invention fluorescent and highly spherical mesoscale sophorolipid mesostructures are optionally magnetic nanoparticles loaded Sophorolipid mesostructures.

In an embodiment of the present invention said mesostructure is useful for bio-imaging and therapeutic applications.

In another embodiment of the present invention the therapeutic applications comprise targeted, drug delivery, controlled drug release, inducing the hyperthermia effect.

In an embodiment, present invention provides a method for synthesis of Fluorescent and highly spherical mesoscale sophorolipid mesostructure as claimed in claim 1 and the said process comprising the steps of:
  i. sonicating the sophorolipid in water in the ratio ranging between 1 mg/ml to 10 mg/ml for period in the range of 3 to 4 hrs;
  ii. irradiating solution of sophorolipid as obtained in step (i) with UV laser pulses for a period in the range of 50 min-60 min to obtain Fluorescent and highly spherical mesoscale sophorolipid mesostructure In yet another embodiment of the present invention the UV laser pulses consisting of wavelength 248 nm, energy density 166 mJ and pulse repetition frequency 10 Hz.

In yet another embodiment of the present invention a simple one step method for synthesis of magnetic Sophorolipid mesostructures comprising:
  a. mixing sophorolipid and $Fe_3O_4$ in the ratio ranging between 10:1 to 5:1 in water followed by sonicating for period in the range of 3 to 4 hrs;
  b. irradiating the solution as obtained in step (a) with UV laser pulses for a period in the range of 50 min-60 min
  c. isolating the magnetic Sophorolipid mesostructures as obtained in step (b) using a magnet.

In yet another embodiment of the present invention the irradiation is conducted at 248 nm wavelength, 150 mJ energy and 10 Hz frequency.

The present inventors have surprisingly found that laser irradiation of Sophorolipid solution yields Sophorolipid mesostructures with great fluorescence.

Present invention provides fluorescent and highly spherical mesoscale sophorolipid mesostructures having size in the range of 100-300 nm, characterized by NMR double triplet signature at δ (ppm): 5.34 as well as at 5.37 in CDCl$_3$, TMS, 400 Hz; an intense peak at 1630 cm$^{-1}$ in FTIR; the characteristic peaks at 130.24 and 130.36 ppm in 13C NMR, indicating the extra C=C bond. These mesoscale sophorolipid molecular assemblies are prepared by a process comprising a) sonicating the sophorolipid in water for 3 to 4 hrs and b) irradiating solution of sophorolipid with UV laser pulses consisting of wavelength 248 nm, energy density 166 mJ and pulse repetition frequency 10 Hz for 60 min.

The pulsed UV laser induced formation of self-assembled vesicular mesostructures of biosynthesized Sophorolipid without the addition of any stabilizing agent, or other organic or inorganic additives. This formation can be viewed as a two step self-assembly process wherein the amphiphile first forms a bilayer which then closes to form a unique spherical morphology.

In another aspect, the invention provides fluorescent, spherical and magnetic nanoparticles loaded Sophorolipid mesostructures useful for bio-imaging and therapeutic applications such as hyperthermia. These magnetic vesicular mesostructures of Sophorolipid can be used in the field of biomedical and pharmaceuticals science. Accordingly, the mesostructures of the instant invention are loaded with magnetic (magnetite) nanoparticles for easy recovery.

Iron oxide nanoparticles ($Fe_3O_4$) based magnetic hyperthermia has been extensively investigated in the field of biomedical and pharmaceuticals science. A major problem has to be solved is to provide sufficiently high concentration of magnetic nanoparticles for bulk solution heating inside the cells.

Accordingly, the invention provides a simple one step method for synthesis of magnetic Sophorolipid mesostructures which comprises a) mixing sophorolipid and $Fe_3O_4$ followed by sonicating for 3 to 4 hrs; b) irradiating the solution with UV laser pulses and c) isolating the magnetic Sophorolipid mesostructures using a magnet. The irradiation is typically conducted at wavelength 248 nm, energy 150 mJ and frequency 10 Hz. The ratio of Sophorolipid to $Fe_3O_4$ nanoparticles may be in the range of 10:1 to 5:1.

Thus the present invention demonstrate that the Sophorolipid mesostructures can be easily loaded with high density magnetite nanoparticles conferring on them the capability to easily fuse with the cell membrane. Such a mesostructure can permeate into cells very effectively at high concentration enabling effective delivery of the load. Most interestingly these Sophorolipid based mesostructures are fluorescent as well, in contrast to the non-fluorescent property of the parent molecules. The fluorescent self-assembled sophorolipid structures are achieved by laser irradiation of the aqueous solution of sophorolipid. Importantly the laser synthesized mesostructures can be easily redispersed in aqueous medium after being dried.

Concurrent fluorescence and magnetism brings further value to these systems in the context of both bio-imaging and targeted drug delivery.

DETAILED DESCRIPTION OF THE INVENTION

In accordance with the above, the instant invention provides novel UV-Laser-synthesized fluorescent, spherical and magnetic nanoparticle loaded Sophorolipid mesostructures and the process for preparation thereof, useful for bio-imaging and therapeutic applications.

Accordingly, in a preferred embodiment, Sophorolipid was synthesized by fermentation using *Candida bombicola* (ATCC 22214) as described elsewhere (I. N. A. Van Bogaert et al. Appl. Microbiol. Biotechnol., 2007). In brief, *Candida bombicola* seed culture was grown in MGYP medium. Then the cells were re-dispersed in production medium containing 10% glucose. This production medium was supplemented with hydrophobic secondary carbon source i.e. oleic acid in absolute ethanol just enough to make a suspension. As a result of reaction between the yeast biomass with glucose and fatty acid, a brown and viscous liquid (SL) could be seen to settle at the bottom of the flask after incubation for 96 to 120 hrs which contains 80% Lactonic form as confirmed by HPLC. This was further purified by reported base hydrolysis method elsewhere (M. Kasture et al., Langmuir, 2007; M. B. Kasture et al. J. Chem. Sci., 2008) to get acidic sophorolipid. While us working on self-assembly of sophorolipid in water reported by Richard Gross et. al. (S. Zhou, C. Xu, J. Wang, W. Gao, R. Akhverdiyeva, V. Shah and R. Gross, Langmuir), the inventors have obtained ribbon like helical structure. The inventors further observed crystal formation in extract when kept in the refrigerator for some time. This form was analyzed by HPLC and concluded that the same is sophorolipid according to references. Crystalline structures thus obtained were separated by centrifugation and washed thrice with ethyl acetate.

In another embodiment, the invention is based on 'green' chemistry, wherein no synthetic chemical steps are used for production of sophorolipid mesostructures. The product formed is completely biodegradable and the end products fatty acid and glucose are non-toxic. Further the sophorolipid used for nano/meso-assemblies is FDA approved and the allowable limit for human uptake is as high as 5 ml kg$^{-1}$ body weight. However there is no stress on the body system if taken in by any route.

Figure 5:
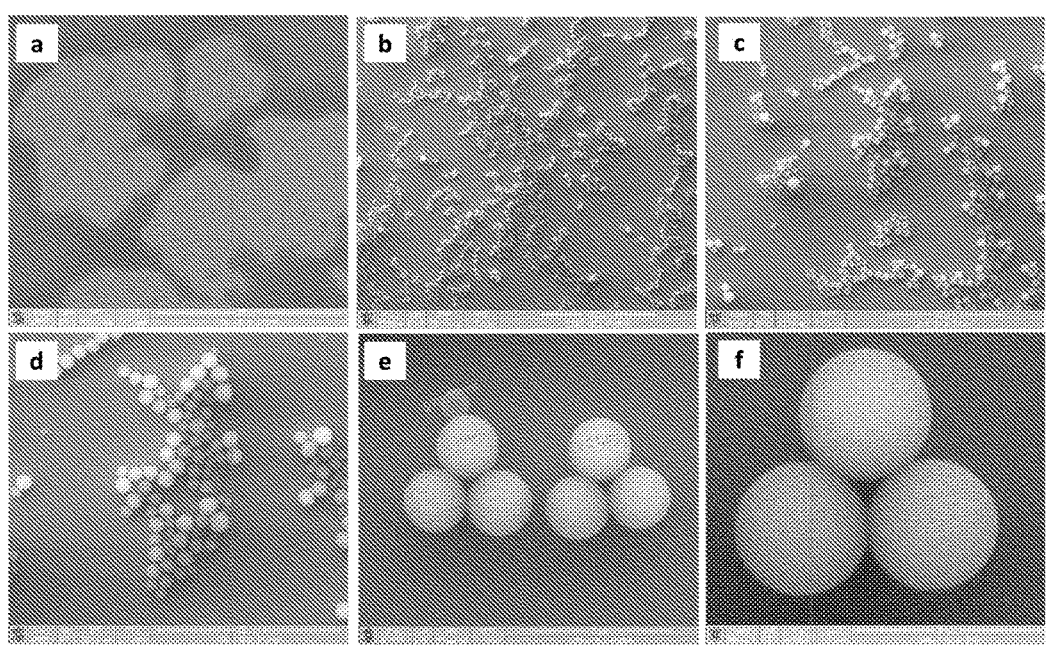
FIG. 5 represents scanning electron microscope image of Sophorolipid mesostructure
  (a) sophorolipid (Acidic) as appear without irradiation;
    (b-f) after laser irradiation (Scale Bar a and d: 40 µm;
      b: 100 µm; c: 50 µm; e: 5 um and f: 3 µm)

In another embodiment, different types of sophorolipids, namely crude, acidic and crystalline form (lactonic SL), were subjected to pulsed excimer laser irradiation (L=248 nm, pulse width 20 ns, energy density 166.67 mJ/cm$^2$). Microscopy studies and other physical characterizations were done for all three samples. When the crude Sophorolipid was processed with laser irradiation mixed population of some spherical microstructures with cloudy tube-like structures were obtained. The lactonic sophorolipid formed undefined hazy structure, where only fibre and tube like structures were seen to form. However in the case of the acidic form of the sophorolipid, which is diacetate in nature, extremely well-defined and fairly uniform spherical mesostructures were formed. The size range of such sophorolipid mesostructures was 0.5-2.5 µm which could be reduced to less than 100 nm by optimizing process parameters such as laser irradiation time, energy and stirring solution. Indeed, an 100 nm size represents an ideal size range for bio-imaging experiments in medical science. (FIG. 5). The reference to sophorolipid in the following sections implies its acidic form unless specifically stated otherwise.

Figure 2:
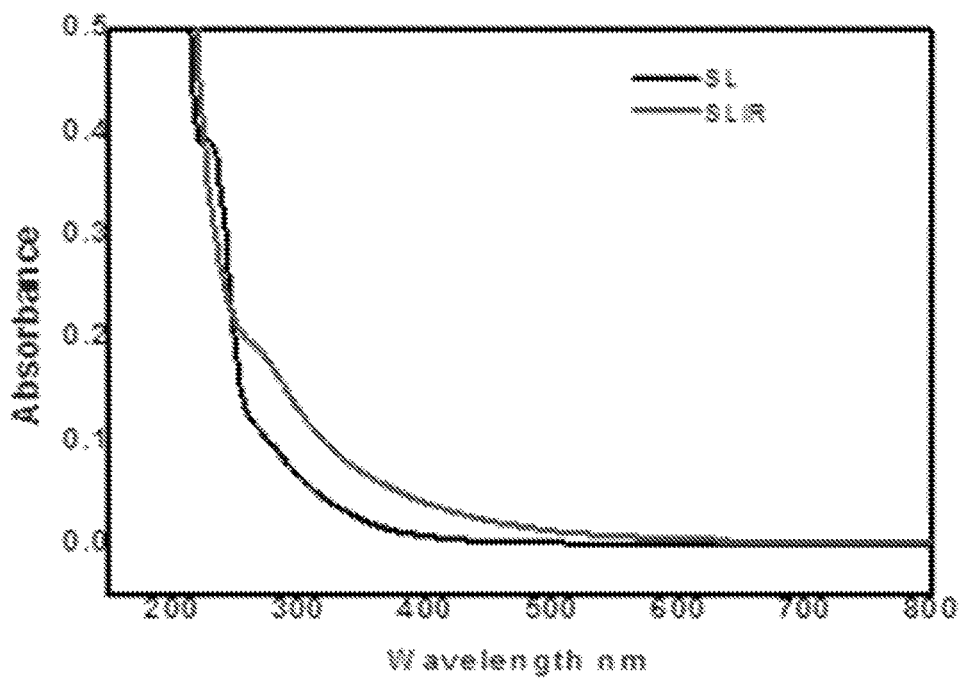
FIG. 2 represents UV-Visible spectra measurement of unirradiated and irradiated Sophorolipid mesostructure.

When 100 µl of unirradiated Sophorolipid and laser irradiated Sophorolipid solutions were taken in 3 ml distilled water they showed marked difference in their appearance to the naked eye. Irradiated Sophorolipid appeared transparent and yellowish whereas, the unirradiated one was milky. After sonicating the Sophorolipid solution the UV absorption peak appeared at 228 nm while it shifted to 278 nm after laser irradiation as clearly seen in FIG. 2.

Figure 3:
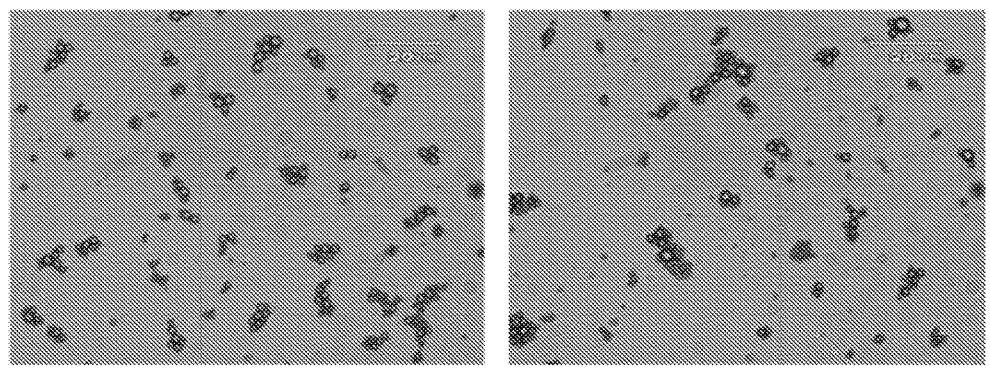
FIG. 3 represents polarized optical microscope image of unirradiated and irradiated Sophorolipid mesostructures.

In another embodiment, polarized microscopic study was done to visualize the ability of laser to make vesicular mesostructures, from the crystalline acidic form of sophorolipid. According to Elisa Zini et al (E. Zini, M. Gazzano and M. Scandola, Macromolecules, 2008) Lactonic sophorolipid can form polymer like structure by ring opening when heat energy was applied for 48 hours using a heat press. In the polarized microscope image FIG. 3 perfect spherical sophorolipid mesostructures were seen in agglomerated form, whereas in the case of Lactonic sophorolipid only ribbon and rods like structure were obtained. To analyze the reason for the formation of these nano-range vesicular structures of sophorolipid the inventors have referred to the work done by Markus Antonietti and Stephan Forster elsewhere (M. Antonietti and S. Forster, Adv. Mater., 2003) where they mention that in order to minimize energy loss, planar sheet like lipid assemblies make spherical structures and tubules.

Figure 4:
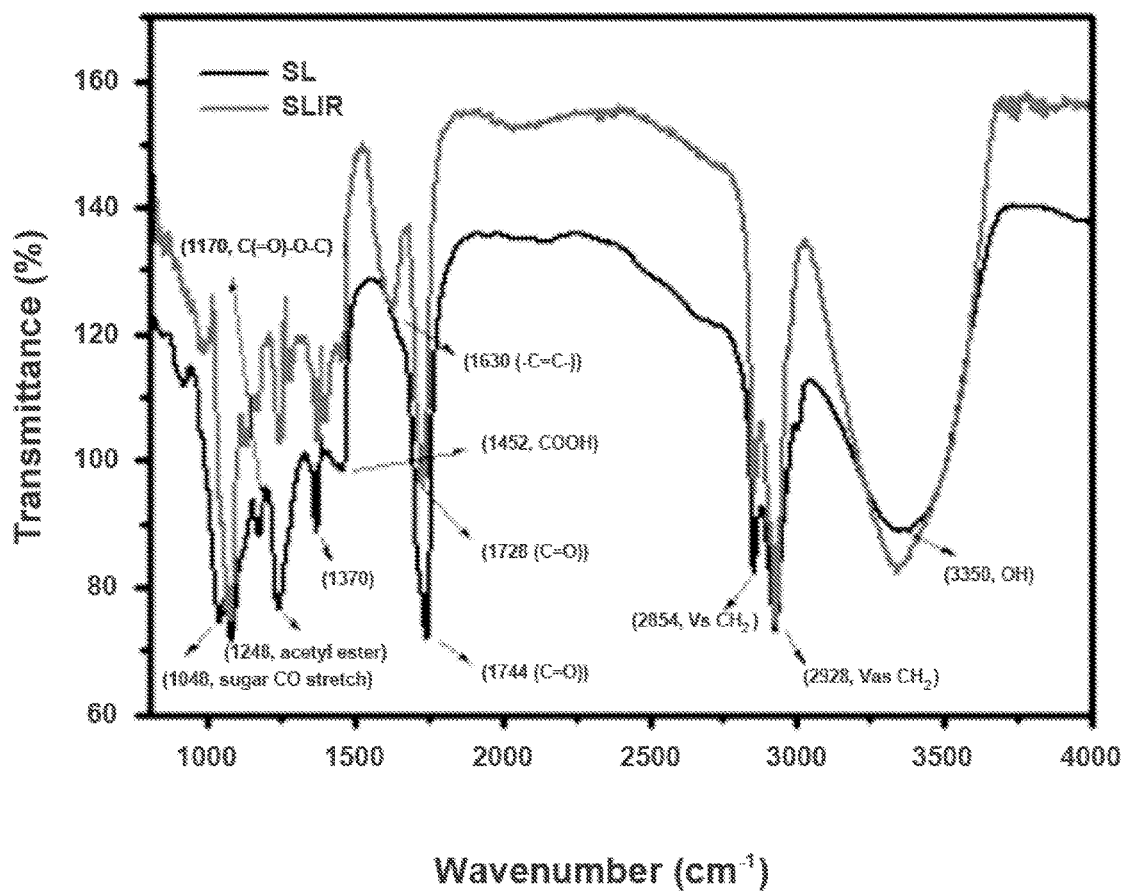
FIG. 4 represents FTIR analysis of unirradiated and irradiated Sophorolipid (acidic) mesostructures.

The Sophorolipid samples, both in unirradiated and laser irradiated forms, were also characterized by FTIR. FIG. 4 shows the FTIR spectra of the unirradiated Sophorolipid, which reveals a broad band at 3350 cm$^{-1}$ corresponding to the O—H stretch in its structure. The spectrum also reveals that asymmetrical stretching (CH$_2$) and symmetrical stretching (CH$_2$) of methylene groups are reflected at 2928 and 2854 cm$^{-1}$, respectively. Lactones and esters have two strong absorption bands arising from C—O and C—O stretching; the C—O absorption band at 1,728 cm$^{-1}$ may include contributions from these groups (lactones, esters, or acids). The stretch of C—O band of C (—O)—O—C in lactones exists at 1,170 cm$^{-1}$, while that from the acetyl esters is found to be at 1,248 cm$^{-1}$. Moreover, sugar C—O stretch of C—O—H groups is found at 1,048 cm$^{-1}$ and the band at 1,452 cm$^{-1}$ corresponds to the C—O—H in-plane bending of carboxylic acid (—COOH) in the structure of the product. All these structural details are similar to those reported in the literature elsewhere (M. B. Kasture et al. J. Chem. Sci., 2008) for acidic SLs, which, therefore, confirmed the fermentation product to be acidic Sophorolipid. Laser irradiated Sophorolipid shows all spectral peaks same as unirradiated sophorolipid except a band at 1624 cm$^{-1}$ which is observed due to stretching of the unsaturated C=C bonds in the Sophorolipid. The band at 1624 cm$^{-1}$ in the laser irradiated Sophorolipid can probably be attributed to a unsaturation in the structure of acidic Sophorolipid (L. Zhang et al. Colloids Surf., A: Physicochem. Eng. Aspects, 2004)

Unirradiated Sophorolipid showed cloudy background and led to sheet like films as shown in the SEM image of FIG. 5 (a), whereas acidic form of Sophorolipid when laser irradiated showed beautiful vesicular mesostructures as depicted in SEM images of FIG. 5 (b-f). SEM images give mesostructure size in the range of 1-2 nm. In order to get smaller structures in the 500-1000 nm range the SL mixture was continuously stirred during laser irradiation for one hour. EDAX analysis (Table 1) of SEM confirmed its pure organic nature and that there was no metal contamination or any other factor playing role in nucleation and mesostructure formation. EDAX analysis does not show presence of any metallic components in these sophorolipid mesostructures. Hydrogen is not detected by EDAX analysis, while the relative carbon and oxygen content was about 88 at % and 12 at %, respectively.

TABLE 1

EDAX (Energy dispersive X-ray spectroscopy) Analysis of Laser Irradiated sophorolipid
Laser irradiated Sophorolipid

| Elem | Wt % | At % | K-Ratio | Z | A | F |
|---|---|---|---|---|---|---|
| CK | 84.71 | 88.07 | 0.6754 | 1.0023 | 0.7954 | 1.0001 |
| OK | 15.29 | 11.93 | 0.0201 | 0.9871 | 0.1335 | 1.0000 |
| Total | 100.00 | 100.00 | | | | |

Figure 6:
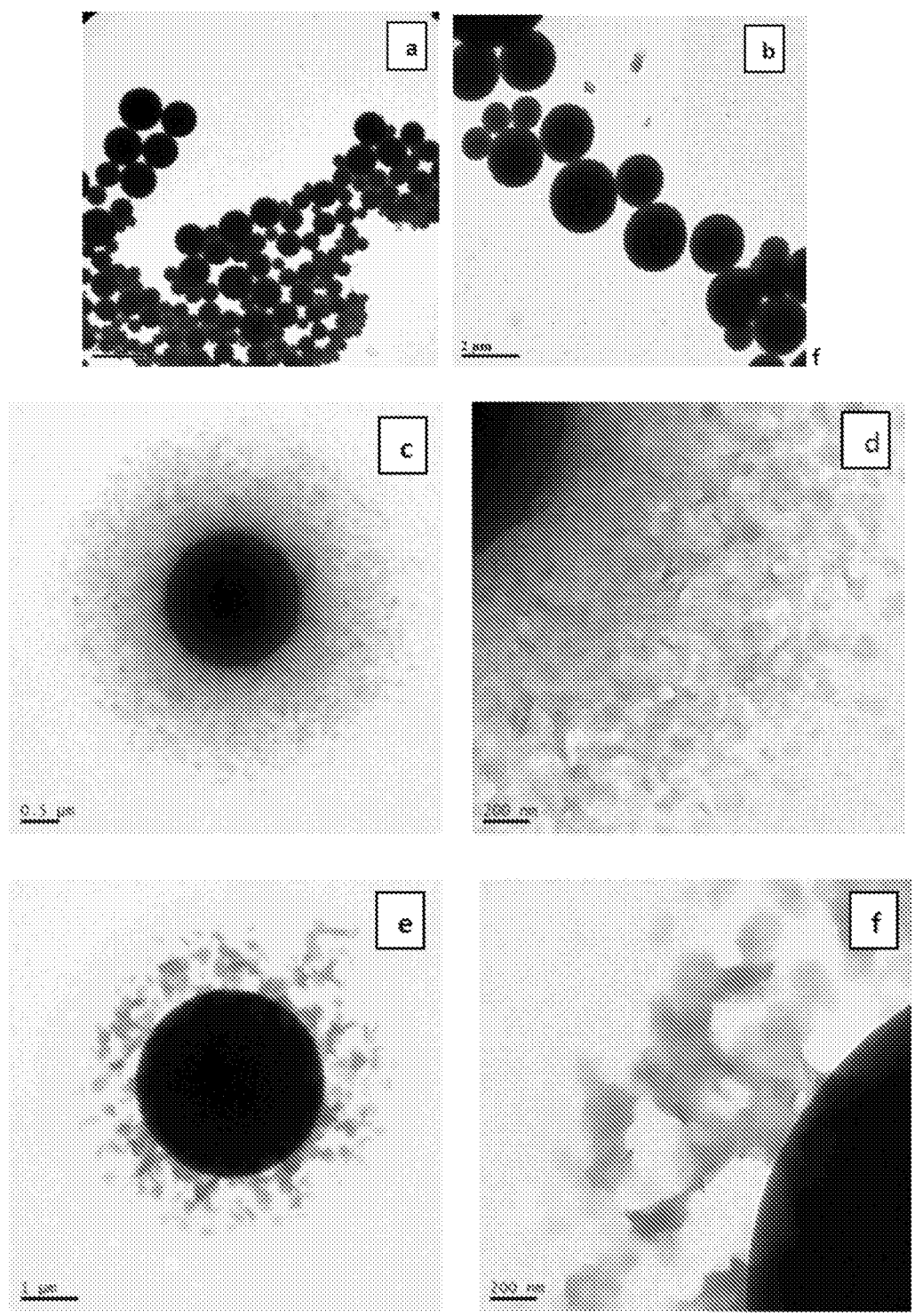
FIG. 6 represents (a, b) TEM images of sophorolipid mesostructures (c, d, e and f) high Resolution Transmission electron HRTEM images of Sophorolipid mesostructures
Figure 7:
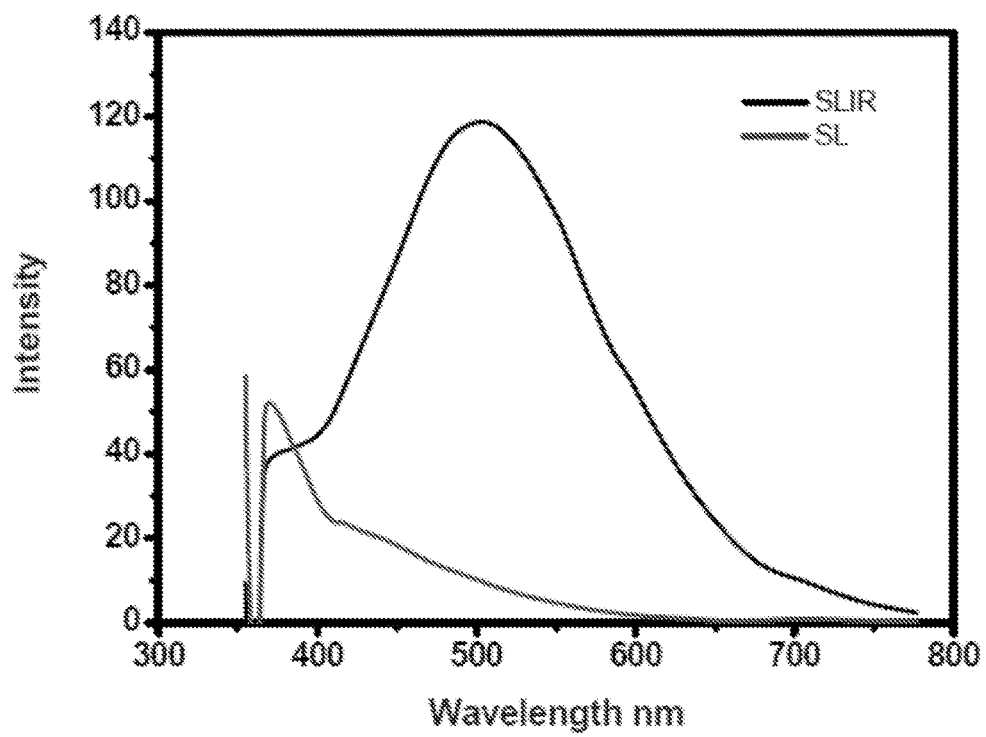
FIG. 7 represents photoluminescence study of irradiated Sophorolipid mesostructures. Define two figures of FIG. 7

Intricate morphological details of these mesostructures could be elucidated by HRTEM (HIGH-RESOLUTION TRANSMISSION ELECTRON MICROSCOPY) analysis. Interesting structures with dense central core and fringes in the outer boundary were observed. These fringes provide these conspicuous structures with increased surface area making them ideal candidates for drug loading studies (FIG. 6).

Figure 8:
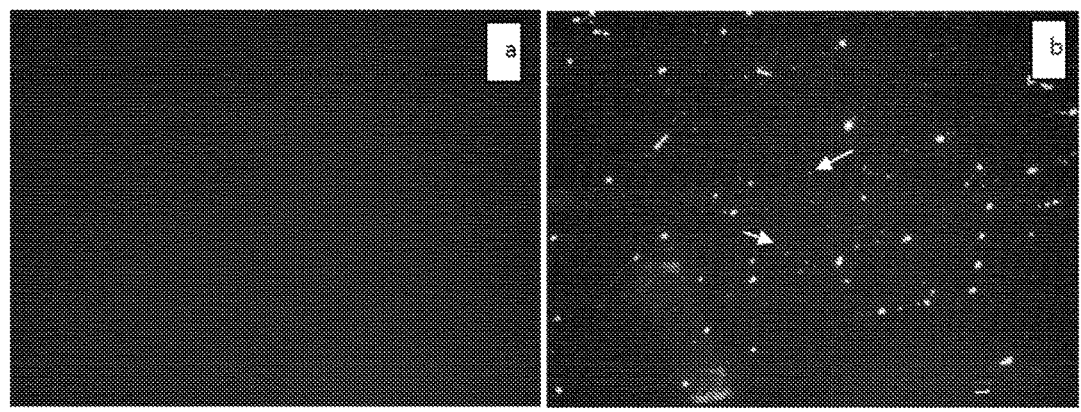
FIG. 8 represents fluorescence Image of (a) unirradiated sophorolipid and (b) irradiated Sophorolipids mesostructures (scale bar 20 µm)
Figure 9:
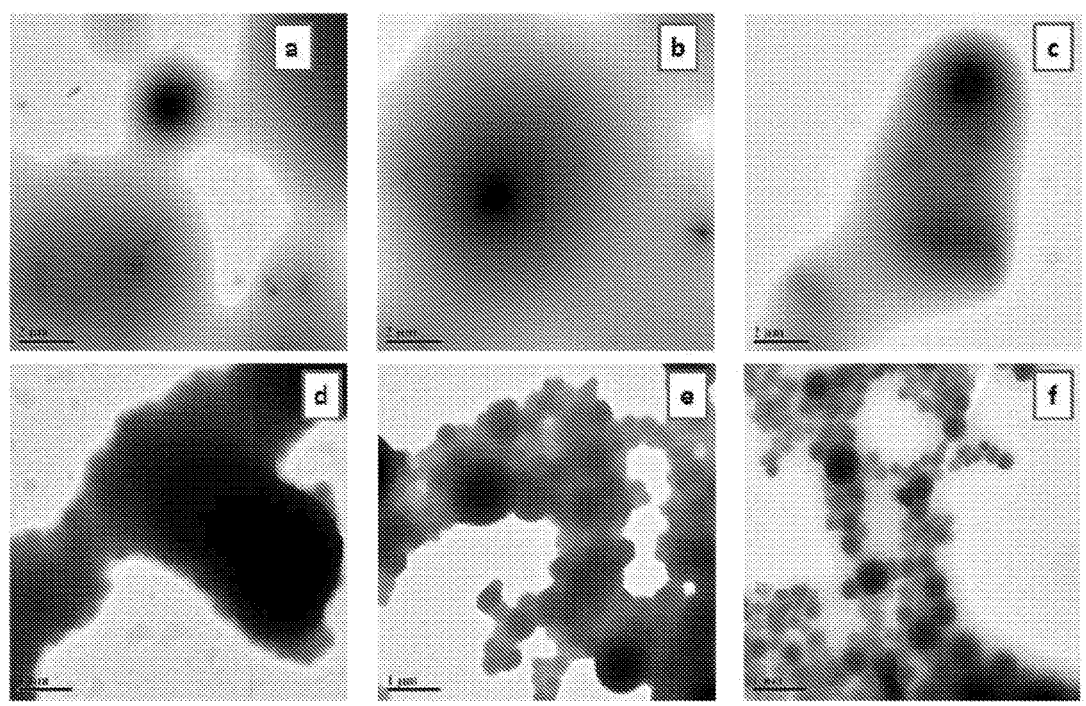
FIG. 9 represents SEM image of Sophorolipid mesostructure formation with increase time: (A) sample collection at before laser irradiation; (B-F) at every 10 minutes interval after laser irradiation (Scale Bar a-c: 2 µm; d-f: 1 µm).

In a further embodiment, photoluminescence study of unirradiated and irradiated sophorolipid was done. Both of these samples were excited at same wavelength i.e. at 330 nm. In case of unirradiated sophorolipid sample it was observed that its emission spectra lies around 370 nm, which belongs to its molecular orbital levels. While in case of irradiated sophorolipid sample its emission enhanced drastically i.e. several times as compared to unirradiated. Also emission spectra of irradiated sample get shifted towards visible region at 500 nm. Further study also confirms regarding the enhancement in the green fluorescence as shown in FIG. 8.

Figure 10:
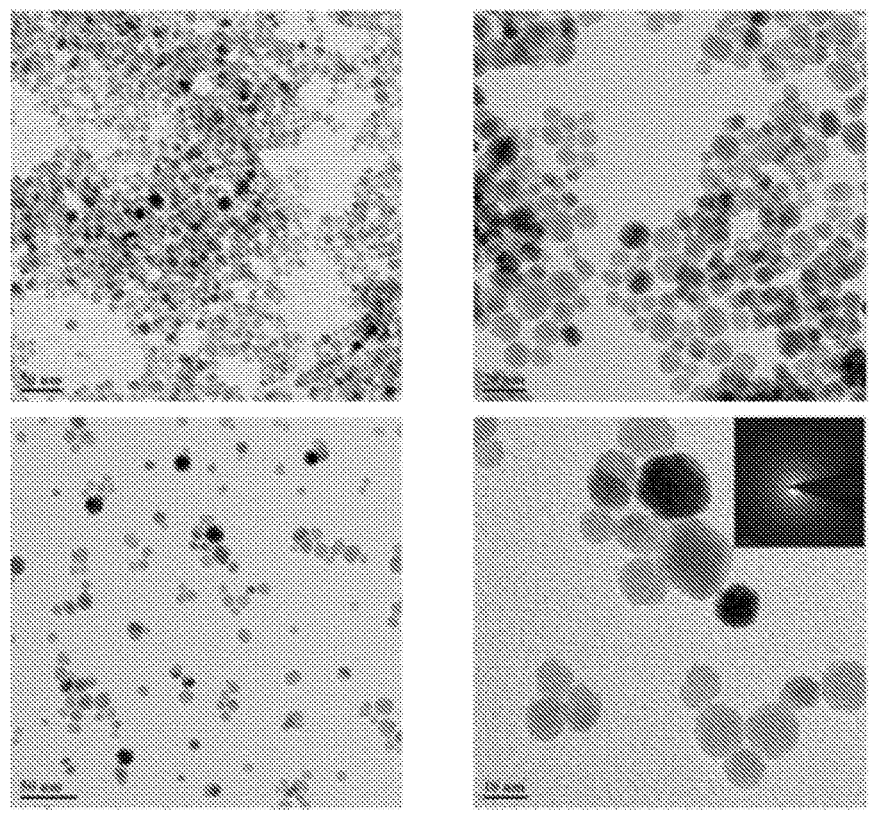
FIG. 10 represents transmission electron microscope (TEM) image of $Fe_3O_4$ Nanoparticles; define different four figures.
Figure 11:
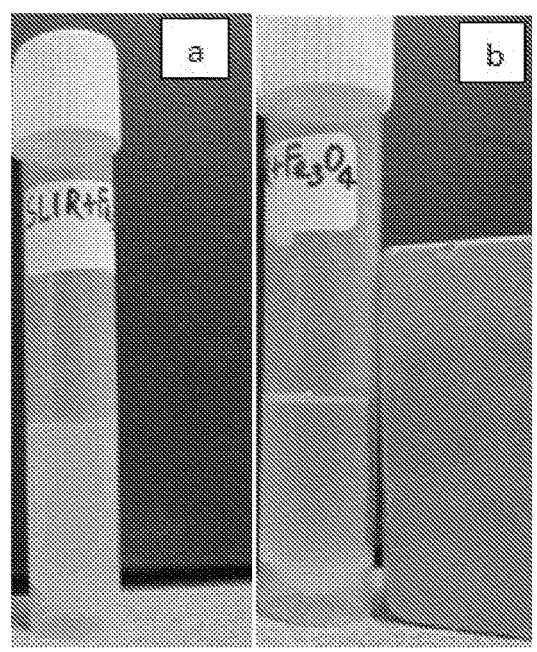
FIG. 11 represents appearance of magnetic Sophorolipid mesostructures without (a) and with (b) magnetic field.

To study the process of pulsed UV laser induced self-assembly of SL (acidic form) kinetic study was performed. Samples were collected at every 10 minutes interval to check for the changes happening during pulsed laser irradiation (FIG. 10). After initial 10 minutes the sheet-like structure of sophorolipid was seen to morph by local shrinking and formation of some defined globule like structures which are seen to be prominent over the hazy mass present. Antonietti and Forster explained the energy conservation in vesicles formation stating that when lipid sheet spreads it form vesicle like structure to minimise it's bending energy (M. Antonietti and S. Forster, Adv. Mater., 2003). The inventors hypothesized that the mesostructure formation of the instant invention follows similar reaction mechanism. Reaction mechanism kinetics shows that during the initial 10 minutes of laser irradiation sophorolipid forms sheet like structure which further condenses during the next 20 minutes. After 40 minutes the lipid sheet starts to form some defined structures and this gets converted into spherical mesostructures in the next 10 minutes. Laser irradiation for one hour provides the energy required for the SL mixture to form spherical structures. Also it was seen that these structures do not form by providing heat energy from any other source and that laser energy was crucial for formation of these sophorolipid mesostructures. By fine tuning the laser energy, time and proportion of Sophorolipid, nanoparticles ranging in size 100-300 nm were obtained.

(linear energy $E_{disk}=2\pi R_D \gamma$)

(bending energy $E_{bend}=8\pi k$)

Iron oxide (Magnetite, $Fe_3O_4$ or Maghemite gamma-$Fe_2O_3$) nanoparticles have long been known to be useful in drug delivery and nano-medicinal applications. However their intrinsic surface area is not that high. Therefore the inventors undertook the task of exploring the possibility of loading them on the highly spherical laser synthesized sophorolipid mesostructures. Needless to mention that this can render them even more biocompatible, especially in so far as their interaction with cells is concerned. Indeed sophorolipids could help facilitate the entry of the iron oxide nanoparticles inside cells since lipids can easily fuse with the cell membrane. Moreover iron oxide impregnated SL particles can be easily directed to a specific site under the influence of an external magnetic field favouring the applicability of this bio-inorganic composite system to cancer hyperthermia.

Accordingly, in yet another embodiment, the invention provides magnetic Sophorolipid mesostructures that are prepared by one pot process. Super-paramagnetic $Fe_3O_4$ nanoparticles were synthesized by polyol method and these were then mixed with Sophorolipid in distilled water and irradiated with UV laser. Iron oxide nanoparticles embedded complex structures of SL were obtained which was easily separable using a magnet. Time kinetics studies were done by adding $Fe_3O_4$ nanoparticles during synthesis of spherical mesostructures at different time intervals. It was observed that when $Fe_3O_4$ nanoparticles were added during synthesis at 0 times, almost all of the particles got embedded in the core of these mesostructures. $Fe_3O_4$ nanoparticles which were added after 20 and 40 minutes during the synthesis of the SL mesostructures, showed more peripheral in their location. These embedded SL structures were smaller and compact in nature when compared to pure SL vesicular mesostructures. Edax Analysis of Laser Irradiated sophorolipid is shown in table 2 at 40 minutes and 50 minutes respectively.

TABLE 2

| Edax Analysis of Laser Irradiated sophorolipid | | | | | | |
|---|---|---|---|---|---|---|
| Elem | Wt % | At % | K-Ratio | Z | A | F |
| SL ($Fe_3O_4$ nanoparticles at min 40) | | | | | | |
| CK | 79.15 | 86.32 | 0.5136 | 1.0098 | 0.6425 | 1.0001 |
| OK | 15.05 | 12.32 | 0.0210 | 0.9945 | 0.1402 | 1.0002 |
| FeL | 5.80 | 1.36 | 0.0171 | 0.8617 | 0.3415 | 1.0000 |
| Total | 100.00 | 100.00 | | | | |
| SL ($Fe_3O_4$ nanoparticles at min 50) | | | | | | |
| CK | 85.57 | 90.83 | 0.6218 | 1.0069 | 0.7216 | 1.0001 |
| OK | 10.33 | 8.23 | 0.0135 | 0.9916 | 0.1314 | 1.0001 |
| FeL | 4.10 | 0.93 | 0.0124 | 0.8592 | 0.3522 | 1.0000 |
| Total | 100.00 | | | | | |

Figure 12:
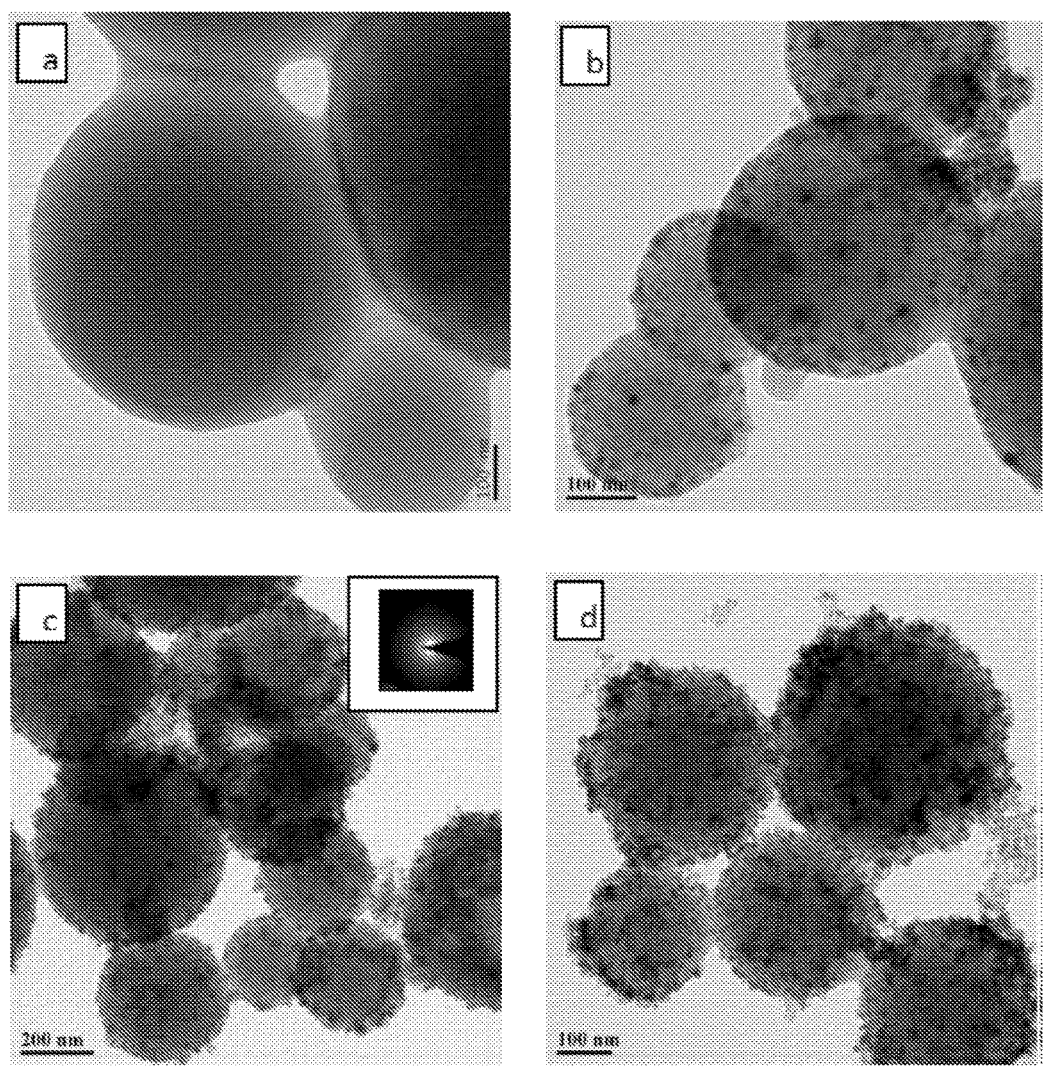
FIG. 12 represents transmission electron microscope (TEM) image of $Fe_3O_4$ embedded Sophorolipid mesostructure at different time interval (a) at 0 minutes (b) at 20 minutes (c) at 40 minutes (d) at 50 minutes.
Figure 13:
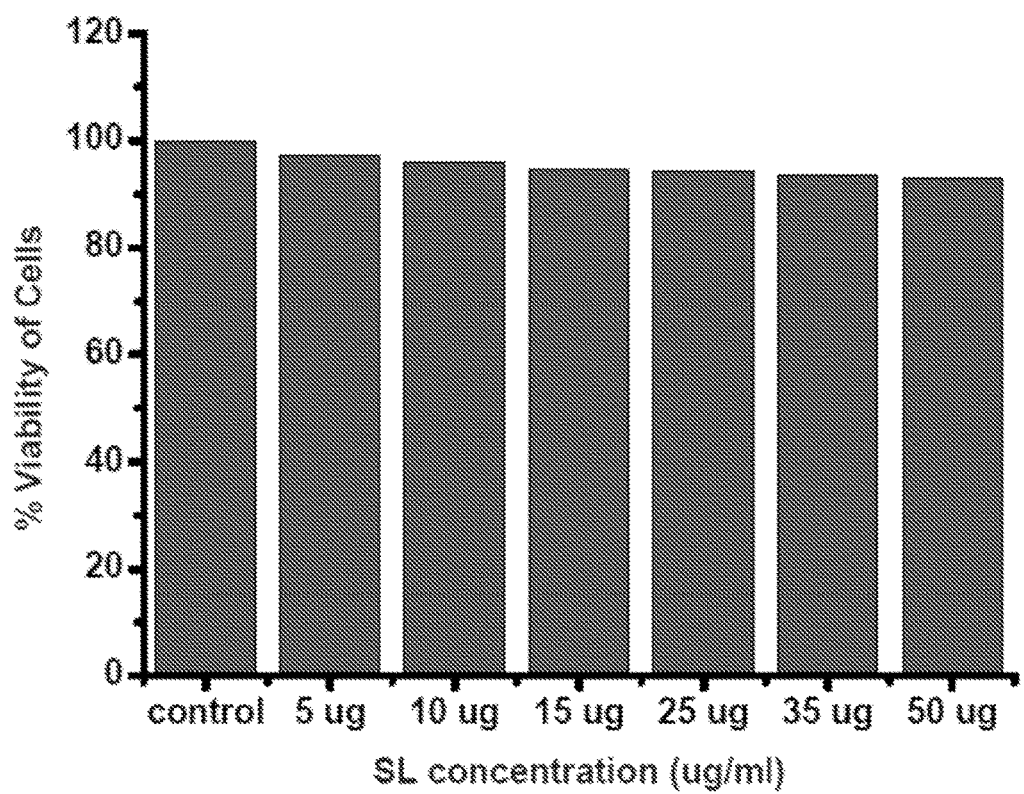
FIG. 13 represents cytotoxicity analysis of Sophorolipid mesostructure.

One pot synthesis of nanoparticles and nanoassemblies of SL was possible by monitoring the time and addition of $Fe_3O_4$ nanoparticle. Depending upon the time interval (FIG. 12) of addition of $Fe_3O_4$ nanoparticles, we can define the shape and size of Sophorolipid nanoassemblies and $Fe_3O_4$ nanoparticles position in the same. To get a particular well-defined shape and size requisite amounts of $Fe_3O_4$ in Sophorolipid mesostructures various combinations were tried as described in materials in methods.

Cyto-Toxicity Analysis of Sophorolipid Mesostructures

Cyto-toxicity analysis of the laser-synthesized sophorolipid mesostructures was done using MTT assay. For this a genetically engineered HeLa derived cell line (tzMbl) was used. Vesicular sophorolipid sample, which had been dried to powder form, was resuspended in sterile distilled water before the assay. Then appropriate concentration of the sample was added to the wells of a 96 well plate and the plate was incubated for 2 days. The viability of cells was then checked by their ability to reduce the tetrazolium salt (MTT) to bluish purple coloured formazan crystals which can be solubilised by acidified propanol and optical density measured at 540 nm. This assay proved to us that the SL mesostructures are not detrimental to the viability of eukaryotic cells even at a concentration of 50 µg/ml.

Thus, according to the present invention, Sophorolipid mesostructures were synthesized using a simple one step method which involved irradiating the solution of sophorolipid with UV laser pulses. There was no involvement of any organic solvent or compound in the synthesis process that would compromise the inherent organic biocompatible nature of the original sophorolipid molecule. The structures were well characterized using a variety of techniques and cytotoxicity assay showed that they were not toxic to living cells even at 50 ug/ml. The invention further demonstrated that the structures thus formed could be impregnated with magnetic iron oxide nanoparticles to make the whole structure ferromagnetic. Interestingly this process also led to eventual reduction in the overall size of then particles. While no luminescence is observed in the case of the original sophorolipid molecules these laser assembled structures were noted to exhibit strong fluoresce when illuminated with visible light and this phenomenon was not influenced by the presence or lack thereof of iron oxide nanoparticles in these structures. This clearly makes them ideal candidates for imaging in-vivo. These extremely cost effective sophorolipid mesostructures can certainly find many applications in drug delivery, bio-imaging and magnetic hyperthermia Animal studies in this regard are under way.

Advantages of Invention

The optical properties, biocompatibility, magnetic property and cost effectiveness make these mesostructures excellent candidates for bio-imaging and other therapeutic applications.

EXAMPLES

The following examples are given by way of illustration therefore should not be construed to limit the scope of the invention.

Material and Methods

Oleic acid Sophorolipid was biosynthesized by incubating *Candida bombicola* in presence of glucose and oleic acid using a method described elsewhere. Sonicator and UV-Vis spectra of Sophorolipid mesostructures were monitored on a Jasco-V-570 UV/Vis/NIR spectrophotometer operated at a resolution of 2 nm. The purified powders of Sophorolipid and Sophorolipid mesostructures were crushed with KBr, pelleted and the Fourier transform infra-red (FTIR) spectra were recorded on a Perkin-Elmer Spectrum-One instrument at a resolution of 4 cm-1. A 248 nm KrF excimer laser (Lambda Physik—Germany) with a maximum average power of 40 watts (pulse energy=150 mJ) and a pulse-width of 20 ns was used in the irradiation process. Scanning electron microscopy (SEM) with Energy-dispersive x-ray spectroscopy (EDX) (FEI Quanta 200 3D) was used for the determination of morphology and elemental composition, respectively. Samples for transmission electron microscopy (TEM) were prepared by drop coating the isolated and re-suspended solution on carbon-coated copper grids. TEM measurements were performed on Tecnai F 30 instrument operated at an accelerating voltage of 300 kV, High resolution-transmission electron microscopy (HR-TEM, FEI Tecnai 300).

Example 1

Production of Sophorolipid

Sophorolipid was prepared by the resting cell method. In the first step adequate cell mass was harvested by growing the *Candida bombicola* (ATCC 22214) in MGYP medium. Then the cells were re-dispersed in production medium containing 10% glucose. This production medium was supplemented with hydrophobic secondary carbon source i.e. oleic acid in absolute alcohol. Oleic acid Sophorolipid was formed as a brown and viscous liquid which was found to settle at the bottom of the flask after 96 hrs provide exact time of incubation. After incubation period the cells were separated from the broth by centrifugation at 5000 rpm, 10° C. for 20 min. The SL formed was extracted from the supernatant with ethyl acetate. To the ethyl acetate phase, anhydrous sodium sulphate was added for removal of residual water, filtered and then ethyl acetate was removed under vacuum. The unconverted fatty acid was removed by washing with n-hexane. The crude sophorolipid thus obtained was purified by column chromatography which was given four different types of sophorolipid forms. Different forms of sophorolipid were analyzed by LCMS (LIQUID CHROMATOGRAPHY MASS SPECTROMETRY), MALDI TOF (MATRIX ASSISTED LASER DESORPTION AND IONIZATION—TIME OF FLIGHT), NMR (NUCLEAR MAGNETIC RESONANCE) and HPLC (HIGH PERFORMANCE LIQUID CHROMATOGRAPHY).

Example 2

Synthesis of Sophorolipid Mesostructures by Laser Irradiation

For synthesis of mesostructures, different concentrations of Sophorolipid (3 mg/ml) were mixed in distilled water and then sonicated for 3 hours. Sophorolipid water emulsion looked visibly turbid after sonication which was then irradiated by Laser pulses (wavelength 248 nm, energy 150 mJ and frequency 10 Hz) for 60 mins. Sample were collected after different time intervals and analysed by polarised optical, scanning electron, transmission electron and high resolution transmission electron microscopies.

Example 3

Polyol Synthesis of $Fe_3O_4$ Nanoparticles

For the synthesis of super paramagnetic $Fe_3O_4$ nanoparticles, 1 mM of iron acetylacetonate was mixed in 30 ml triethylene glycol and sonicated for 5 minutes in the presence of argon gas. A round bottom flask was kept in silicon oil bath and the temperature was raised (2° C./min) to 278° C. After 30 minutes at constant temp (278° C.) the product was cooled to (25° C.) and then thoroughly washed with ethyl acetate and separated by magnet. It was dried 12 hrs in an oven at 50° C.

Example 4

Synthesis of $Fe_3O_4$ Impregnated Sophorolipid Mesostructures

For synthesis of $Fe_3O_4$ encapsulated Sophorolipid mesostructures, different concentrations of Sophorolipid (3 mg/ml) sophorolipid and $Fe_3O_4$ (0.6 mg/ml) nanoparticles were mixed in double distilled water and sonicated for 3 hours. After sonication Sophorolipid and $Fe_3O_4$ solution appeared light brown and turbid, which was then irradiated by UV laser pulses (wavelength 248 nm, energy 150 mJ and frequency 10 Hz). It was found that 5:1 ratio of Sophorolipid to $Fe_3O_4$ nanoparticles gave highly reproducible result. Sample were collected after different time intervals and analyzed by different techniques stated above. 70% of sophorolipid convert to fluorescence sophorolipid mesostructures.

Example 5

Fluorescence Study

This was carried out by observing the prepared samples under a fluorescence microscope. 10 micro-liter sample was taken on a clean glass slide and a coverslip was put on it. The sample was excited at wavelength 330 nm and green colored fluorescence was observed. Also the sample was observed using confocal microscopy and fluorescent nanoparticles of similar intensity were observed.

Example 6

Physical and Chemical Characterization
UV-Vis Studies

UV-Vis absorption spectra were recorded on Varian CARY 100 Bio UV-Vis spectrophotometer respectively, with 10 mm quartz cell at 25±0.1° C. For spectra of, 100 µl SL and SLIR solution was prepared by diluted to 3 ml with distilled water. The solution of this, mixed gently and subsequently spectra was recorded.

FTIR Analysis

The structures of unirradiated and irradiated SL mesostructures were analyzed by FTIR spectroscopy in transmission mode using a Nicolet Magna IR-750 spectrophotometer at 4 cm-1 resolution with 64 scans between 4000 and 400 cm-1. Two milligram of dried powder was mixed with 198 milligram KBr and analysed by instrument.

NMR Study 1H and 13C NMR spectra were recorded on BrukerAvance DPX 200 and DPX 400 instruments operating at 400 MHz (1H) and 100 MHz (13C) frequencies.

MALDI-MS Study

A MALDI-MS study of the unirradiated and irradiated samples was done on an AB SCIEX TOF/TOF 5800 instrument. For the measurements 5 µl of the sample was mixed with 20 µl of the dithranol matrix.

Microscopic Studies

Polarized microscopic study—Samples were imaged with an Polarized microscope, that was used to know the initial structural study sophorolipid mesostructure. 10 µl sample was place on a glass slide and put cover slip on that. Kept for dry then study under microscope.

Scanning Electron Microscopy (SEM)—Field emission scanning electron microscopy images acquired on FEI QUANTA 200 microscope, equipped with a tungsten filament gun, operating at WD 10.6 mm and 20 kV. A 10 µL aliquot of SL and SLIR solution nanoparticles were placed on silicon wafer and fixed on copper stubs with help of carbon tape. The samples were dried at room temperature for overnight and imaged were taken without gold coating.

Fluorescence Study

This was carried out by observing the prepared samples under a fluorescence microscope. 10 µL samples were taken on a clean glass slide and a coverslip was put on it. The sample was excited at 330 nm (excitation optimized) and green colored fluorescence was observed. Also the sample was observed using confocal microscopy and fluorescent nanoparticles of similar intensity were observed.

Cytotoxicity Analysis of Sophorolipid Mesostructures

HeLa cells were grown in RPMI 1640 (Gibco, INVITROGEN) supplemented with 10% v/v fetal bovine serum (Gibco, INVITROGEN), 2 mM L-glutamine, 100 U ml-1 penicillin, and 100 µg ml-1 streptomycin (all from Sigma-Aldrich, USA) and maintained at 37° C. and 5% of CO2. For the actual MTT assay, cells were grown in commercially available 96 well cell culture plates (AXYGEN). Samples were prepared in sterile distilled water and appropriate concentrations were added to each of the wells and each test sample concentration was tested in triplicate.

A set of five control wells which did not contain the test compound were also maintained to eliminate any bias from the experimental design. Cells were incubated with varying concentrations of the vesicular mesostructures for a period of 48 hours after which the spent medium was withdrawn from the wells and 90 µl of fresh complete culture medium was added. To this 10 µl of MTT (Sigma Aldrich) stock solution of 10 mg ml-1 was added and incubated at 37° C. under 5% CO2 for a period of 4 hours. After the incubation period the reduced formazan crystals were dissolved with acidified propanol and then optical density was measured at 540 nm using a BioRad microplate reader. The intensity of purple color developed indicated the extent of viability of the cells after incubation with the test compound.

The Hyperthermia Experiment

The RF hyperthermia experiment was performed with a 365 kHz RF power source and a Pancack coil. A magnetic SL mesostructure (25 mg ml-1 sophorolipid assembly sample with 5 mg ml-1 Fe3O4 nanoparticles) was used for the experiment. The data were collected at different time intervals for both the SL and magnetic SL mesostructure samples.

We claim:

1. A fluorescent and spherical mesoscale sophorolipid mesostructure having a size in the range of 100-300 nm, wherein the mesostructure exhibits a nuclear magnetic resonance (NMR) double triplet signature at 5.34 and 5.37 ppm, in $CDCl_3$ and tetramethylsilane (TMS), and at 400 Hz; an intense peak at 1630 $cm^{-1}$ in Fourier transform infrared spectroscopy (FTIR); and characteristic peaks at 130.24 and 130.36 ppm in $^{13}C$ NMR, which indicate an extra C=C bond.

2. The fluorescent and spherical mesoscale sophorolipid mesostructure as claimed in claim 1, loaded with magnetic nanoparticles.

3. A method of bio-imaging comprising:
   introducing the sophorolipid mesostructures as claimed in claim 1 into a biological sample;
   illuminating the sophorolipid mesostructures with light such that they fluoresce; and
   imaging the fluorescent sophorolipid mesostructures.

4. A method for synthesis of the fluorescent and spherical mesoscale sophorolipid mesostructure as claimed in claim 1 comprising:
   i. sonicating the sophorolipid in water, wherein the concentration of the sophorolipid is from 1 mg/ml to 10 mg/ml for period of 3 to 4 hrs;
   ii. irradiating a solution of sophorolipid, as obtained in step (i), with UV laser pulses for a period of 50 min-60 min to obtain the fluorescent and spherical mesoscale sophorolipid mesostructure.

5. The method according to claim 4, wherein the UV laser pulses have a wavelength of 248 nm, an energy density of 166 mJ and a pulse repetition frequency of 10 Hz.

6. A one step method for synthesis of magnetic Sophorolipid mesostructures comprising:
   a. mixing sophorolipid and $Fe_3O_4$ in a ratio of 10:1 to 5:1, respectively, in water, followed by sonicating for period of 3 to 4 hrs;
   b. irradiating the solution, as obtained in step (a), with UV laser pulses for a period of 50 min-60 min; and
   c. isolating the magnetic Sophorolipid mesostructures, as obtained in step (b), using a magnet.

7. The method according to claim 6, wherein the irradiating is conducted at a wavelength of 248 nm, an energy density of 150 mJ and a frequency of 10 Hz.

8. A therapeutic method comprising administering a fluorescent and spherical mesoscale sophorolipid mesostructure as claimed in claim 1 to a subject.

9. The therapeutic method as claimed in claim 8, wherein the fluorescent and spherical mesoscale sophorolipid mesostructure mediates targeted drug delivery, controlled drug release, and/or induces a hyperthermia effect.

* * * * *